US008501408B2

(12) United States Patent
Trama et al.

(10) Patent No.: US 8,501,408 B2
(45) Date of Patent: Aug. 6, 2013

(54) **METHODS AND COMPOSITIONS FOR DETECTING AND IDENTIFYING SPECIES OF *CANDIDA***

(75) Inventors: Jason Trama, Burlington, NJ (US); Martin E. Adelson, Hillsborough, NJ (US); Eli Mordechai, Robbinsville, NJ (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 679 days.

(21) Appl. No.: 11/321,984

(22) Filed: Dec. 29, 2005

(65) Prior Publication Data

US 2008/0102449 A1 May 1, 2008

Related U.S. Application Data

(60) Provisional application No. 60/641,914, filed on Jan. 6, 2005.

(51) Int. Cl.
*C12Q 1/68* (2006.01)

(52) U.S. Cl.
USPC ........................................................ 435/6.12

(58) Field of Classification Search
None
See application file for complete search history.

(56) References Cited

U.S. PATENT DOCUMENTS

| | | | |
|---|---|---|---|
| 6,210,891 B1 | 4/2001 | Nyren et al. | |
| 6,258,568 B1 | 7/2001 | Nyren | |
| 2003/0104372 A1 | 6/2003 | Ahmadian et al. | |

OTHER PUBLICATIONS

Li et al. (Eur. J. Clin. Microbiol. Infect. Dis., 2003, vol. 22, p. 693-696).*
Guiver et al. (J. Clin. Pathology, 2001, vol. 54, p. 362-366).*
Chen et al. (Journal of Clinical Microbiology, 2000, vol. 38, No. 6, p. 2302-2310).*
Buck et al. (Biotechniques, 1999, 23(5), p. 528-536).*
Pastinen et al. (Clinical Chemistry, 1996, vol. 42, No. 9, p. 1391-1397).*
Diaz-Guerra et al. (Journal of Clinical Microbiology, 1997, vol. 35, No. 4, p. 856-861).*
Sequence alignments—SEQ ID No:3 and SEQ ID No:7, p. 4, 2008.*
Guiver alignment—p. 2, 2008.*
Lott et al. (Yeast, 1993, 9(11):1199-1206).*
Troell et al. (Int. J. Parasitology, 2003, vol. 33, p. 765-771).*
National Center for Biotechnology Information (NCBI) accession No. L47112 (*Candida tropicalis* 18S ribosomal RNA gene, 3' end, 5.8S ribosomal RNA gene, complete, 28S ribosomal RNA gene, 5' end), Oct. 1999.
National Center for Biotechnology Information (NCBI) accession No. L11352 (*Candida parapsilosis* 5.8S ribosomal RNA gene), Sep. 1994.
National Center for Biotechnology Information (NCBI) accession No. AF218994 (*Candida glabrata* strain UWFP-108 5.8S ribosomal RNA gene, partial sequence; internal transcribed spacer 2, complete sequence; 28S ribosomal RNA gene, partial sequence).
National Center for Biotechnology Information (NCBI) accession No. L07796 (*Candida albicans* CBS2730 5.8S ribosomal RNA gene).

Trama et al. (2005) Detection and identification of *Candida* species associated with *Candida vaginitis* by real-time PCR and pyrosequencing. Mol Cell Probes 19:145-152.
Ronaghi et al. (1998) A sequencing method based on real-time pyrophosphate. Science 281:363, 365.
Chen et al. (2000) Identification of medically important yeasts using PCR-based detection of DNA sequence polymorphisms in the internal transcribed spacer 2 region of the rRNA genes. J Clin Microbiol 38:2302-2310.
Luo et al. (2002) Rapid identification of pathogenic fungi directly from cultures by using multiplex PCR. J Clin Microbiol 40:2860-2865.
Evertsson et al. (2000) Detection and identification of fungi in blood using broad-range 28S rDNA PCR amplification and species-specific hybridization. Apmis 108:385-392.
Tamura et al. (2000) New PCR primer pairs specific for *Candida dubliniensis* and detection of the fungi from the *Candida albicans* clinical isolates in Japan. Clin Lab 46:33-40.
Wahyuningsih et al. (2000) Simple and rapid detection of *Candida albicans* DNA in serum by PCR for diagnosis of invasive candidiasis. J Clin Microbiol 38:3016-3021.
Elie et al. (1998) Rapid identification of *Candida* species with species-specific DNA probes. J Clin Microbiol 36:3260-3265.
Holland et al. (1991) Detection of specific polymerase chain reaction product by utilizing the 5'-3' exonuclease activity of Thermus aquaticus DNA polymerase. Proc Natl Acad Sci USA 88:7276-7280.
Guiver et al. (2001) Rapid identification of *Candida* species by Taq-Man PCR. J Clin Pathol 54:362-366.
Borst et al. (2001) Detection of *Candida* spp. in blood cultures using nucleic acid sequence-based amplification (NASBA), Diagn Microbiol Infect Dis 39:155-160.
Shin et al. (1999) Rapid identification of up to three *Candida* species in a single reaction tube by a 5' exonuclease assay using fluorescent DNA probes. J Clin Microbiol 37:165-170.
Selvarangan et al. (2003) Rapid identification of commonly encountered *Candida* species directly from blood culture bottles, J Clin Microbiol 41:5660-5664.
Vilgalys Laboratory. Duke University. Publication date unknown. Conserved primer sequences for PCR amplification and sequencing from nuclear ribosomal RNA. http://www.biology.duke.edu/fungi/mycolab/primers.htm.
Fujita et al. (1995) Microtitration plate enzyme immunoassay to detect PCR-amplified DNA from *Candida* species in blood. J Clin Microbiol 33:962-967.
Trama et al. (2005) Detection of *Candida* species in vaginal samples in a clinical laboratory setting. Infectious Diseases in Obstetrics and Gynecology 13(2):63-67.
Trama et al. Novel technique for identification of vulvovaginal candidiasis by real-time PCR and pyrosequencing. American College of Obstetricians and Gynecologists 52nd Annual Clinical Meeting, May 1-5, 2004, Philadelphia, PA.
Mordechai et al. Prevalency of *Candida* species associated with *Candida vaginitis* in the United States. American Society for Microbiology 104th General Meeting, May 23-27, 2004, New Orleans, LA, Poster C-108.

* cited by examiner

*Primary Examiner* — Stephanie K Mummert
(74) *Attorney, Agent, or Firm* — Siu K. Lo

(57) ABSTRACT

Methods and compositions useful in the detection and identification of species of *Candida* are disclosed. The compositions are combinations of oligonucleotides, where the forward primers of the primer pairs have identical sequences, while each reverse primer of the primer pairs has a unique sequence relative to all of the other reverse primers; or the reverse primers of the primer pairs have identical sequences, while each forward primer of the primer pairs has a unique sequence relative to all of the other forward primers. The oligonucleotides also include probes capable of detecting these amplicons, and sequencing primers for determining, in primer extension reactions, the nucleotide sequences contained within the amplicons. The detection of an amplicon indicates that the sample contains at least one isolate of *Candida albicans, Candida glabrata, Candida parapsilosis,* or *Candida tropicalis,* and the nucleotide sequence data is used to determine which of these four *Candida* species is present.

23 Claims, 3 Drawing Sheets

A

B

C

D

E

F

G

H

SEQUENCE LISTING

<160> NUMBER OF SEQ ID NOS: 29

<210> SEQ ID NO 1
<211> LENGTH: 261
<212> TYPE: DNA
<213> ORGANISM: Candida albicans

<400> SEQUENCE: 1

```
gcatcgatga agaacgcagc gaaatgccga tacgtaatat gaattgcaga tatccgtgaa      60
tcatcgaatc tttgaacgca cattgcgccc tctggtattc cggagggcat gcctgtttga     120
gcgtcgtttc tccctcaaac cgctgggttt ggtgttgagc aatacgactt gggtttgctt     180
gaaagacggt agtggtaagg cgggatcgct ttgacaatgg cttaggtcta accaaaaaca     240
ttgcttgcgg cggtaacgtc c                                               261
```

<210> SEQ ID NO 2
<211> LENGTH: 261
<212> TYPE: DNA
<213> ORGANISM: Candida albicans

<400> SEQUENCE: 2

```
ggacgttacc gccgcaagca atgttttgg ttagacctaa gccattgtca aagcgatccc       60
gccttaccac taccgtcttt caagcaaacc caagtcgtat tgctcaacac caaacccagc     120
ggtttgaggg agaaacgacg ctcaaacagg catgccctcc ggaataccag agggcgcaat     180
gtgcgttcaa agattcgatg attcacggat atctgcaatt catattacgt atcggcattt     240
cgctgcgttc ttcatcgatg c                                               261
```

<210> SEQ ID NO 3
<211> LENGTH: 298
<212> TYPE: DNA
<213> ORGANISM: Candida glabrata

<400> SEQUENCE: 3

```
gcatcgatga agaacgcagc gaaatgcgat acgtaatgtg aattgcagaa ttccgtgaat      60
catcgaatct ttgaacgcac attgcgccct ctggtattcc gggggcatg cctgtttgag     120
cgtcatttcc ttctcaaaca cgttgtgttt ggtagtgagt gatactctcg tttttgagtt     180
aacttgaaat tgtaggccat atcagtatgt gggacacgag cgcaagcttc tctattaatc     240
tgctgctcgt ttgcgcgagc ggcgggggtt aatactgtat taggttttac caactcgg      298
```

<210> SEQ ID NO 4
<211> LENGTH: 298
<212> TYPE: DNA
<213> ORGANISM: Candida glabrata

<400> SEQUENCE: 4

```
ccgagttggt aaaacctaat acagtattaa cccccgccgc tcgcgcaaac gagcagcaga      60
ttaatagaga agcttgcgct cgtgtcccac atactgatat ggcctacaat ttcaagttaa     120
ctcaaaaacg agagtatcac tcactaccaa acacaacgtg tttgagaagg aaatgacgct     180
caaacaggca tgcccccccgg aataccagag ggcgcaatgt gcgttcaaag attcgatgat     240
tcacggaatt ctgcaattca cattacgtat cgcatttcgc tgcgttcttc atcgatgc      298
```

<210> SEQ ID NO 5
<211> LENGTH: 251
<212> TYPE: DNA
<213> ORGANISM: Candida parapsilosis

<400> SEQUENCE: 5

```
gcatcgatga agaacgcagc gaaatgccga taagtaatat gaattgcaga tattcgtgaa      60
tcatcgaatc tttgaacgca cattgcgccc tttggtattc caaagggcat gcctgtttga     120
gcgtcatttc tccctcaaac cctcgggttt ggtgttgagc gatacgctgg gtttgcttga     180
aagaaaggcg gagtataaac taatggatag gttttttcca ctcattggta caaactccaa     240
aacttcttcc a                                                         251
```

<210> SEQ ID NO 6
<211> LENGTH: 251
<212> TYPE: DNA
<213> ORGANISM: Candida parapsilosis

<400> SEQUENCE: 6

```
tggaagaagt tttggagttt gtaccaatga gtggaaaaaa cctatccatt agtttatact      60
ccgcctttct ttcaagcaaa cccagcgtat cgctcaacac caaacccgag ggtttgaggg     120
agaaatgacg ctcaaacagg catgcccttt ggaataccaa agggcgcaat gtgcgttcaa     180
agattcgatg attcacgaat atctgcaatt catattactt atcggcattt cgctgcgttc     240
ttcatcgatg c                                                         251
```

<210> SEQ ID NO 7
<211> LENGTH: 247
<212> TYPE: DNA
<213> ORGANISM: Candida tropicalis

<400> SEQUENCE: 7

```
gcatcgatga agaacgcagc gaaatgcgat acgtaatatg aattgcagat attcgtgaat      60
catcgaatct tgaacgcac attgcccct tggtattcc aaagggcatg cctgtttgag       120
cgtcatttct cccccaaacc cccgggtttg gtgttgagca atacctagg tttgtttgaa      180 agaatttacg tggaaactta ttttaagcga cttaggttta tccaaaacgc ttattttgct     240
agtggcc                                                              247
```

<210> SEQ ID NO 8
<211> LENGTH: 247
<212> TYPE: DNA
<213> ORGANISM: Candida tropicalis

<400> SEQUENCE: 8

-continued

```
ggccactagc aaaataagcg ttttggataa acctaagtcg cttaaaataa gtttccacgt      60
aaattctttc aaacaaacct agggtattgc tcaacaccaa acccgggggt ttgggggaga     120
aatgacgctc aaacaggcat gcccttttgga ataccaaagg gggcaatgtg cgttcaaaga    180
ttcgatgatt cacgaatatc tgcaattcat attacgtatc gcatttcgct gcgttcttca    240
tcgatgc                                                               247
```

<210> SEQ ID NO 9
<211> LENGTH: 22
<212> TYPE: DNA
<213> ORGANISM: Candida albicans

<400> SEQUENCE: 9

```
ggacgttacc gccgcaagca at                                               22
```

<210> SEQ ID NO 10
<211> LENGTH: 31
<212> TYPE: DNA
<213> ORGANISM: Candida glabrata

<400> SEQUENCE: 10

```
ccgagttggt aaaacctaat acagtattaa c                                     31
```

<210> SEQ ID NO 11
<211> LENGTH: 25
<212> TYPE: DNA
<213> ORGANISM: Candida parapsilosis

<400> SEQUENCE: 11

```
tggaagaagt tttggagttt gtacc                                            25
```

<210> SEQ ID NO 12
<211> LENGTH: 25
<212> TYPE: DNA
<213> ORGANISM: Candida tropicalis

<400> SEQUENCE: 12

```
ggccactagc aaaataagcg ttttg                                            25
```

<210> SEQ ID NO 13
<211> LENGTH: 20
<212> TYPE: DNA
<213> ORGANISM: Candida

<400> SEQUENCE: 13

```
gcatcgatga agaacgcagc                                                  20
```

<210> SEQ ID NO 14
<211> LENGTH: 25
<212> TYPE: DNA
<213> ORGANISM: Candida

<400> SEQUENCE: 14

```
aaaygacgct caaacaggca tgccc                                            25
```

<210> SEQ ID NO 15
<211> LENGTH: 25
<212> TYPE: DNA
<213> ORGANISM: Candida

<400> SEQUENCE: 15

```
gggcatgcct gtttgagcgt crttt                                            25
```

```
<210> SEQ ID NO 16
<211> LENGTH: 20
<212> TYPE: DNA
<213> ORGANISM: Candida albicans

<400> SEQUENCE: 16
acgttaccgc cgcaagcaat                                              20

<210> SEQ ID NO 17
<211> LENGTH: 20
<212> TYPE: DNA
<213> ORGANISM: Candida glabrata

<400> SEQUENCE: 17
cgagttggta aaacctaata                                              20

<210> SEQ ID NO 18
<211> LENGTH: 25
<212> TYPE: DNA
<213> ORGANISM: Candida parapsilosis

<400> SEQUENCE: 18
tggaagaagt tttggagttt gtacc                                        25

<210> SEQ ID NO 19
<211> LENGTH: 21
<212> TYPE: DNA
<213> ORGANISM: Candida tropicalis

<400> SEQUENCE: 19
ggccactagc aaaataagcg t                                            21

<210> SEQ ID NO 20
<211> LENGTH: 33
<212> TYPE: DNA
<213> ORGANISM: Candida albicans

<400> SEQUENCE: 20 gttttttggtt agacctaagc cattgtcaaa gcg                              33

<210> SEQ ID NO 21
<211> LENGTH: 29
<212> TYPE: DNA
<213> ORGANISM: Candida glabrata

<400> SEQUENCE: 21
cagtattaac ccccgccgct cgcgcaaac                                    29

<210> SEQ ID NO 22
<211> LENGTH: 32
<212> TYPE: DNA
<213> ORGANISM: Candida parapsilosis

<400> SEQUENCE: 22
aatgagtgga aaaacctat ccattagttt at                                 32

<210> SEQ ID NO 23
<211> LENGTH: 35
<212> TYPE: DNA
<213> ORGANISM: Candida tropicalis

<400> SEQUENCE: 23
tttggataaa cctaagtcgc ttaaaataag tttcc                             35
```

```
<210> SEQ ID NO 24
<211> LENGTH: 62
<212> TYPE: DNA
<213> ORGANISM: Candida

<400> SEQUENCE: 24 gcttttagg gtttaagtta aaccccccct aaggcccag ctttgctgcc aaaggccaaa     60
gc                                                                 62

<210> SEQ ID NO 25
<211> LENGTH: 65
<212> TYPE: DNA
<213> ORGANISM: Candida

<400> SEQUENCE: 25
aagttttttg ggttaaggta ggcctaaaaa aaagccccta atttgcctac ttaaaaggct   60
ttagt                                                              65

<210> SEQ ID NO 26
<211> LENGTH: 68
<212> TYPE: DNA
<213> ORGANISM: Candida

<400> SEQUENCE: 26
gttttttttg gggttaagta aaccccctta aaaggcctac ttggctttaa aactaaaaag   60
gctttgcc                                                           68

<210> SEQ ID NO 27
<211> LENGTH: 61
<212> TYPE: DNA
<213> ORGANISM: Candida

<400> SEQUENCE: 27
aactaggtaa gtttaaggcc cccaaaaaag cccctagctt cccagcttag gctttaaaac   60
t                                                                  61

<210> SEQ ID NO 28
<211> LENGTH: 64
<212> TYPE: DNA
<213> ORGANISM: Candida

<400> SEQUENCE: 28
ctttagggta atttaaaaac ccccctaag gcctgcctgc cttaaaagct aaggctttaa    60
accc                                                               64

<210> SEQ ID NO 29
<211> LENGTH: 67
<212> TYPE: DNA
<213> ORGANISM: Candida

<400> SEQUENCE: 29
aattttggga agttaaaggc ctaaaaaaaa gccttactgc ccttaaaaat ttaaaggttt   60
tttacct                                                            67
```

METHODS AND COMPOSITIONS FOR DETECTING AND IDENTIFYING SPECIES OF *CANDIDA*

CROSS REFERENCES TO RELATED APPLICATIONS

The present application claims benefit, under 35 U.S.C. 119(e), to U.S. Provisional Application No. 60/641,914, entitled "Speciation of *Candida* associated with *Candida Vaginitis* by Pyrosequencing" filed on Jan. 6, 2005, the entire contents of which are hereby incorporated by reference.

BACKGROUND OF THE INVENTION

1. Field of the Invention

The present invention is broadly concerned with methods and compositions useful for detecting and identifying species of *Candida*. More particularly, the present invention relates to methods in which oligonucleotides are used as forward and reverse primers in polymerase chain reactions using nucleic acids from biological samples as templates, as probes for detecting any resultant amplicon, and as nucleotide sequencing primers to determine whether any resultant amplicon is specific to *Candida albicans, Candida glabrata, Candida parapsilosis*, or *Candida tropicalis*, thereby allowing one to ascertain whether the sample contains any of these isolates.

2. Description of the Related Art

Vaginal candidiasis causes 20% to 25% of infectious *vaginitis* cases, second only to the 40% to 50% of cases caused by bacterial vaginosis (see Sobel, 1997, Vaginitis, N Engl J Med 337:1896-1903). *Candida vaginitis* (CV) is marked by pruritis, soreness, a change in discharge, dyspareunia, vulvar erythema, edema, and fissures (see Sobel, 1997, Vaginitis, N Engl J Med 337:1896-1903; and Diagnosis of *Candida vaginitis,* 1985, J Fam Pract 20(1):19-20). The condition is rare before puberty, but by the age of 25, nearly one-half of all women will have had at least one clinician-diagnosed episode of CV. Overall, it is estimated that 75% of all women will experience an episode of CV in their lifetime (see Sobel, 1997, Vaginitis, N Engl J Med 337:1896-1903; and Sobel, 1988, Pathogenesis and epidemiology of vulvovaginal candidiasis, Ann N Y Acad Sci 544:547-557). Among the *Candida* species causing infections, *Candida albicans, Candida glabrata, Candida parapsilosis*, and *Candida tropicalis* account for 80% to 90% of fungal isolates encountered worldwide (see Pfaller, 1996, Nosocomial candidiasis: emerging species, reservoirs, and modes of transmission, Clin Infect Dis 22(2):S89-S94; and Hazen et al., 2003, Comparison of the susceptibilities of *Candida* spp. to fluconazole and voriconazole in a 4-year global evaluation using disk diffusion, J Clin Microbiol 41:5623-5632). Although *Candida albicans* is implicated in 85% to 95% of all cases of CV (see Sobel, 1997, Vaginitis, N Engl J Med 337:1896-1903; and Sobel, 1999, Vulvovaginitis in healthy women, Compr Ther 25:335-346), the widespread use of azole antifungal drugs is postulated to have promoted the shifting of vaginal colonization and selection of more naturally resistant species, such as *Candida glabrata* (see Pfaller et al., 2003, Activities of fluconazole and voriconazole against 1,586 recent clinical isolates of *Candida* species determined by Broth microdilution, disk diffusion, and Etest methods: report from the ARTEMIS Global Antifungal Susceptibility Program, 2001 J Clin Microbiol 41:1440-1446; Snydman, 2003, Shifting patterns in the epidemiology of nosocomial *Candida* infections, Chest 123:500S-503S; Hazen, 1995, New and emerging yeast pathogens, Clin Microbiol Rev 8:462-478; and Fidel et al., 1999, *Candida glabrata*: review of epidemiology, pathogenesis, and clinical disease with comparison to *C. albicans*, Clin Microbiol Rev 12:80-96). Knowledge of the infecting species is highly predictive of likely drug susceptibility and should be used as a guide for selecting therapy (see Pappas et al., 2004, Guidelines for treatment of candidiasis, Clin Infect Dis 38:161-189). Therefore, rapid and specific identification of *Candida* species would facilitate appropriate antifungal selection and improve patient care.

Commonly, *Candida* in vaginal samples is identified by microscopic examination of a wet mount with potassium hydroxide. This technique detects budding yeast cells in only 50% to 70% of women with CV (see Elliott, 1998, Managing patients with vulvovaginal candidiasis, Nurse Pract 23:44-46, 49-53; and 1996, ACOG technical bulletin. Vaginitis. Number 226-July 1996 (replaces No. 221, March 1996). Committee on Technical Bulletins of the American College of Obstetricians and Gynecologists, Int J Gynaecol Obstet 54:293-302) and may fail to detect species other than *Candida albicans* (see 1996, ACOG technical bulletin. Vaginitis. Number 221-March 1996 (replaces no. 135, November 1989). American College of Obstetricians and Gynecologists, Int J Gynaecol Obstet 53:271-280). Alternatively, *Candida albicans* and *Candida tropicalis* can be distinguished by growth on chromogenic agar medium and other species of *Candida* can be identified by enzymatic tests. However, each of these tests requires isolated organisms to be grown on solid medium for 24 to 48 hours before they can be performed or interpreted (see Odds et al., 1994, CHROMagar *Candida*, a new differential isolation medium for presumptive identification of clinically important *Candida* species, J Clin Microbiol 32:1923-1929; and Warren et al., 1995, Cryptococcus, and other yeasts of medical importance, in: P. R. Murray, E. J. Barton, M. A. Pfaller, F. C. Tenover, and R. H. Yolken (Eds.), Manual of clinical microbiology, American Society for Microbiology, Washington, DC, pp. 723-737). In addition, the "gold standard" for definitive biochemical identification requires analysis of assimilation and fermentation, taking up to 30 days to complete (see Warren et al., 1995, Cryptococcus, and other yeasts of medical importance, in: P. R. Murray, E. J. Barton, M. A. Pfaller, F. C. Tenover, and R. H. Yolken (Eds.), Manual of clinical microbiology, American Society for Microbiology, Washington, DC, pp. 723-737).

In recent years, numerous DNA-based techniques have been developed to improve the identification of *Candida* species. Amplification of *Candida* target DNA by the polymerase chain reaction (PCR) is particularly promising because of its simplicity, specificity, and sensitivity (see Chen et al., 2000, Identification of medically important yeasts using PCR-based detection of DNA sequence polymorphisms in the internal transcribed spacer 2 region of the rRNA genes, J Clin Microbiol 38:2302-2310; Luo et al., 2002, Rapid identification of pathogenic fungi directly from cultures by using multiplex PCR, J Clin Microbiol 40:2860-2865; Evertsson et al., 2000, Detection and identification of fungi in blood using broad-range 28S rDNA PCR amplification and species-specific hybridisation, Apmis 108:385-392; Tamura et al., 2000, New PCR primer pairs specific for *Candida dubliniensis* and detection of the fungi from the *Candida albicans* clinical isolates in Japan, Clin Lab 46:33-40; Wahyuningsih et al., 2000, Simple and rapid detection of *Candida albicans* DNA in serum by PCR for diagnosis of invasive candidiasis, J Clin Microbiol 38:3016-3021; and Elie et al., 1998, Rapid identification of *Candida* species with species-specific DNA probes, J Clin Microbiol 36:3260-3265). However, these strategies require post-amplification analyses and are considered to have lower sensitivity than real-time PCR techniques that directly monitor amplification via fluorescent probes (see Holland et al., 1991, Detection of specific polymerase chain reaction product by utilizing the 5'-3' exonuclease activity of *Thermus aquaticus* DNA polymerase, Proc Natl Acad Sci USA 88:7276-7280). Real-time PCR strategies have been developed to identify *Candida* species (see Guiver et al., 2001, Rapid identification of *Candida* species by TaqMan PCR, J Clin Pathol 54:362-366; Borst et al., 2001, Detection of *Candida*spp. in blood cultures using nucleic acid sequence-based amplification (NASBA), Diagn Microbiol Infect Dis 39:155-160; Shin et al., 1999, Rapid identification of up to three *Candida* species in a single reaction tube by a 5' exonuclease assay using fluorescent DNA probes, J Clin Microbiol 37:165-170; and Selvarangan et al., 2003, Rapid identification of commonly encountered *Candida* species directly from blood culture bottles, J Clin Microbiol 41:5660-5664), but these methods were designed and optimized for detection of *Candida* in blood or blood culture. Strategies for the detection of *Candida* species in DNA extracted from vaginal samples, especially without time-consuming culture, are lacking. In addition, current DNA-based *Candida* detection methods do not take into account the fact that DNA sequencing is generally accepted as the most precise method for discriminating among closely related species.

BRIEF SUMMARY OF THE INVENTION

General Overview of the Present Invention

The aforementioned drawbacks in the detection of species of *Candida* are avoided by the two methods of the present invention. Specifically, in each of these methods, a sample (e.g., a biological sample such as a vaginal secretion) is tested for the presence of an isolate of *Candida albicans*, *Candida glabrata*, *Candida parapsilosis*, or *Candida tropicalis* by attempting to generate amplicons specific to one or more of these isolates using oligonucleotides as primers in a polymerase chain reaction. Each amplicon may be detected using an oligonucleotide as a probe. Additionally, each amplicon may be identified by determining its nucleotide sequence. The nucleotide sequence of each amplicon may be determined individually by conducting a single nucleotide sequencing reaction in a vessel. Alternatively, a composite nucleotide sequence composed of the nucleotide sequences of multiple amplicons may be generated by conducting a plurality of nucleotide sequencing reactions in a single vessel. Each nucleotide sequencing reaction may employ an oligonucleotide as a sequencing primer which is extended during the reaction. The present invention also is directed to three compositions (e.g., reaction mixtures or kits) utilized in the methods of the present invention, wherein each of the compositions contains a combination of oligonucleotides, and each oligonucleotide is useful either as a probe, or as a primer for a polymerase chain reaction or a nucleotide sequencing reaction.

The First Method of the Present Invention

The first method of the present invention is a method for determining whether a sample contains an isolate of *Candida albicans*, *Candida glabrata*, *Candida parapsilosis*, or *Candida tropicalis*, wherein the method comprises (a) providing a vessel containing (1) a nucleic acid from the sample, (2) at least two primers selected from the group consisting of first, second, third, and fourth primers, and (3) a fifth primer, wherein the first and fifth primers are capable of priming, in a polymerase chain reaction, the synthesis of a first amplicon specific to the isolate of *Candida albicans*, and wherein the first and fifth primers are not capable of priming, in the polymerase chain reaction, the synthesis of an amplicon specific to the isolate of *Candida glabrata*, *Candida parapsilosis*, or *Candida tropicalis*; wherein the second and fifth primers are capable of priming, in the polymerase chain reaction, the synthesis of a second amplicon specific to the isolate of *Candida glabrata*, and wherein the second and fifth primers are not capable of priming, in the polymerase chain reaction, the synthesis of an amplicon specific to the isolate of *Candida albicans*, *Candida parapsilosis*, or *Candida tropicalis*; wherein the third and fifth primers are capable of priming, in the polymerase chain reaction, the synthesis of a third amplicon specific to the isolate of *Candida parapsilosis*, and wherein the third and fifth primers are not capable of priming, in the polymerase chain reaction, the synthesis of an amplicon specific to the isolate of *Candida albicans*, *Candida glabrata*, or *Candida tropicalis*; wherein the fourth and fifth primers are capable of priming, in the polymerase chain reaction, the synthesis of a fourth amplicon specific to the isolate of *Candida tropicalis*, and wherein the fourth and fifth primers are not capable of priming, in the polymerase chain reaction, the synthesis of an amplicon specific to the isolate of *Candida albicans*, *Candida glabrata*, or *Candida parapsilosis*, and wherein the nucleotide sequences of the first, second, third, and fourth amplicons diverge from each other, (b) incubating the vessel under conditions allowing production of (1) the first amplicon if the sample contains the isolate of *Candida albicans*, (2) the second amplicon if the sample contains the isolate of *Candida glabrata*, (3) the third amplicon if the sample contains the isolate of *Candida parapsilosis*, or (4) the fourth amplicon if the sample contains the isolate of *Candida tropicalis*, and (c) determining that the sample contains (1) the isolate of *Candida albicans* if the first amplicon is produced in (b), (2) the isolate of *Candida glabrata* if the second amplicon is produced in (b), (3) the isolate of *Candida parapsilosis* if the third amplicon is produced in (b), or (4) the isolate of *Candida tropicalis* if the fourth amplicon is produced in (b); or determining that the sample does not contain any of the isolates of *Candida albicans*, *Candida glabrata*, *Candida parapsilosis*, and *Candida tropicalis* if none of the first, second, third, and fourth amplicons are produced in (b).

In a preferred embodiment, in (b), the first primer is capable of hybridizing to at least a portion of a segment of the plus strand of the first amplicon, and the segment consists of nucleotides 240-261 of SEQ ID NO:1; the second primer is capable of hybridizing to at least a portion of a segment of the plus strand of the second amplicon, and the segment consists of nucleotides 268-298 of SEQ ID NO:3; the third primer is capable of hybridizing to at least a portion of a segment of the plus strand of the third amplicon, and the segment consists of nucleotides 227-251 of SEQ ID NO:5; the fourth primer is capable of hybridizing to at least a portion of a segment of the plus strand of the fourth amplicon, and the segment consists of nucleotides 223-247 of SEQ ID NO:7; and the fifth primer is capable of hybridizing to at least a portion of a segment of the minus strand of each of the first, second, third, and fourth amplicons, and the segment consists of nucleotides 242-261 of SEQ ID NO:2.

Advantageously, the first primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters (see below), and the segment consists of nucleotides 240-261 of SEQ ID NO:1; the second primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 268-298 of SEQ ID NO:3; the third primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 227-251 of SEQ ID NO:5; the fourth primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 223-247 of SEQ ID NO:7; and the fifth primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 242-261 of SEQ ID NO:2.

Pairwise nucleotide sequence alignments and determination of percent identities are performed using the default parameters of the Clustal V algorithm or the Clustal W algorithm, wherein both algorithms are incorporated into the Power Macintosh MegAlign 6.1 program (DNASTAR, Madison, Wis.). The default parameters for pairwise alignments using the Clustal V algorithm are as follows: Ktuple=1, gap penalty=3, window=5, and diagonals=5. The default parameters for pairwise alignments using the Clustal W algorithm are as follows: gap penalty=10.00 and gap length=0.10. The Clustal V algorithm is described in Higgins et al., 1989, Fast and sensitive multiple sequence alignments on a microcomputer. Computer Applications in the Biosciences 5:151-153. The Clustal W algorithm is described in Thompson et al., 1994, CLUSTAL W: improving the sensitivity of progressive multiple sequence alignment through sequence weighting, position specific gap penalties and weight matrix choice. Nucleic Acids Research 22:4673-80.

Preferably, the plus strand of the first amplicon comprises the nucleotide sequence of SEQ ID NO:1 and the minus strand of the first amplicon comprises the nucleotide sequence of SEQ ID NO:2; the plus strand of the second amplicon comprises the nucleotide sequence of SEQ ID NO:3 and the minus strand of the second amplicon comprises the nucleotide sequence of SEQ ID NO:4; the plus strand of the third amplicon comprises the nucleotide sequence of SEQ ID NO:5 and the minus strand of the third amplicon comprises the nucleotide sequence of SEQ ID NO:6; and the plus strand of the fourth amplicon comprises the nucleotide sequence of SEQ ID NO:7 and the minus strand of the fourth amplicon comprises the nucleotide sequence of SEQ ID NO:8. More preferably, the plus strand of the first amplicon consists of the nucleotide sequence of SEQ ID NO:1 and the minus strand of the first amplicon consists of the nucleotide sequence of SEQ ID NO:2; the plus strand of the second amplicon consists of the nucleotide sequence of SEQ ID NO:3 and the minus strand of the second amplicon consists of the nucleotide sequence of SEQ ID NO:4; the plus strand of the third amplicon consists of the nucleotide sequence of SEQ ID NO:5 and the minus strand of the third amplicon consists of the nucleotide sequence of SEQ ID NO:6; and the plus strand of the fourth amplicon consists of the nucleotide sequence of SEQ ID NO:7 and the minus strand of the fourth amplicon consists of the nucleotide sequence of SEQ ID NO:8.

Each of the first, second, third, and fourth amplicons preferably is specific to a ribosomal RNA gene such as a ribosomal RNA gene encoding a 5.8S ribosomal RNA, and more preferably is specific to an internal transcribed spacer of a ribosomal RNA gene such as an internal transcribed spacer 2.

Advantageously, each of the first, second, third, and fourth primers is a forward primer, and the fifth primer is a reverse primer; or each of the first, second, third, and fourth primers is a reverse primer, and the fifth primer is a forward primer. Each of the first, second, third, fourth, and fifth primers preferably is from 8 to 50 nucleotides long, and more preferably is from 12 to 24 nucleotides long.

Preferably, the first primer comprises the nucleotide sequence of SEQ ID NO:9, the second primer comprises the nucleotide sequence of SEQ ID NO:10, the third primer comprises the nucleotide sequence of SEQ ID NO:11, the fourth primer comprises the nucleotide sequence of SEQ ID NO:12, and the fifth primer comprises the nucleotide sequence of SEQ ID NO:13. More preferably, the first primer consists of the nucleotide sequence of SEQ ID NO:9, the second primer consists of the nucleotide sequence of SEQ ID NO:10, the third primer consists of the nucleotide sequence of SEQ ID NO:11, the fourth primer consists of the nucleotide sequence of SEQ ID NO:12, and the fifth primer consists of the nucleotide sequence of SEQ ID NO:13.

In another preferred embodiment, the method further comprises detecting the first, second, third, or fourth amplicon using an oligonucleotide probe. The oligonucleotide probe preferably is from 15 to 50 nucleotides long, and more preferably is from 25 to 35 nucleotides long. The oligonucleotide probe is preferably included in the vessel in (b).

In another preferred embodiment, in (b), the oligonucleotide probe is capable of hybridizing to at least a portion of a segment of the plus strand of the first amplicon, and the segment consists of nucleotides 105-129 of SEQ ID NO:1; the oligonucleotide probe is capable of hybridizing to at least a portion of a segment of the plus strand of the second amplicon, and the segment consists of nucleotides 104-128 of SEQ ID NO:3; the oligonucleotide probe is capable of hybridizing to at least a portion of a segment of the plus strand of the third amplicon, and the segment consists of nucleotides 105-129 of SEQ ID NO:5; and the oligonucleotide probe is capable of hybridizing to at least a portion of a segment of the plus strand of the fourth amplicon, and the segment consists of nucleotides 104-128 of SEQ ID NO:7.

Advantageously, the oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 105-129 of SEQ ID NO:1, nucleotides 104-128 of SEQ ID NO:3, nucleotides 105-129 of SEQ ID NO:5, or nucleotides 104-128 of SEQ ID NO:7.

In another preferred embodiment, in (b), the oligonucleotide probe is capable of hybridizing to at least a portion of a segment of the minus strand of the first amplicon, and the segment consists of nucleotides 133-157 of SEQ ID NO:2; the oligonucleotide probe is capable of hybridizing to at least a portion of a segment of the minus strand of the second amplicon, and the segment consists of nucleotides 171-195 of SEQ ID NO:4; the oligonucleotide probe is capable of hybridizing to at least a portion of a segment of the minus strand of the third amplicon, and the segment consists of nucleotides 123-147 of SEQ ID NO:6; and the oligonucleotide probe is capable of hybridizing to at least a portion of a segment of the minus strand of the fourth amplicon, and the segment consists of nucleotides 120-144 of SEQ ID NO:8.

Advantageously, the oligonucleotide probe is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 133-157 of SEQ ID NO:2, nucleotides 171-195 of SEQ ID NO:4, nucleotides 123-147 of SEQ ID NO:6, or nucleotides 120-144 of SEQ ID NO:8.

The oligonucleotide probe preferably comprises the nucleotide sequence of SEQ ID NO:14 or SEQ ID NO:15, and more preferably consists of the nucleotide sequence of SEQ ID NO:14 or SEQ ID NO:15.

In another preferred embodiment, the method further comprises isolating the plus or minus strand of the first, second, third, or fourth amplicon. Preferably, the method further comprises determining the nucleotide sequence of at least a portion of the plus or minus strand of the first, second, third, or fourth amplicon. More preferably, the method further comprises determining the nucleotide sequence by conducting a nucleotide sequencing reaction using a sequencing primer capable of hybridizing, in the nucleotide sequencing reaction, to the plus or minus strand of the first, second, third, or fourth amplicon, wherein the sequencing primer is extended during the nucleotide sequencing reaction. Most preferably, the method further comprises determining the nucleotide sequence of at least the portion of the minus strand of the first, second, third, or fourth amplicon using a first, second, third, or fourth sequencing primer, respectively. The sequencing primer preferably is from 8 to 30 nucleotides long, and more preferably is from 10 to 25 nucleotides long.

In another preferred embodiment, the first sequencing primer is capable of hybridizing, in the nucleotide sequencing reaction, to at least a portion of a segment of the plus strand of the first amplicon, and the segment consists of nucleotides 240-259 of SEQ ID NO:1; the second sequencing primer is capable of hybridizing, in the nucleotide sequencing reaction, to at least a portion of a segment of the plus strand of the second amplicon, and the segment consists of nucleotides 278-297 of SEQ ID NO:3; the third sequencing primer is capable of hybridizing, in the nucleotide sequencing reaction, to at least a portion of a segment of the plus strand of the third amplicon, and the segment consists of nucleotides 227-251 of SEQ ID NO:5; and the fourth sequencing primer is capable of hybridizing, in the nucleotide sequencing reaction, to at least a portion of a segment of the plus strand of the fourth amplicon, and the segment consists of nucleotides 227-247 of SEQ ID NO:7.

Advantageously, the first sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 240-259 of SEQ ID NO:1; the second sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 278-297 of SEQ ID NO:3; the third sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 227-251 of SEQ ID NO:5; and the fourth. sequencing primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 227-247 of SEQ ID NO:7.

Preferably, the first sequencing primer comprises the nucleotide sequence of SEQ ID NO:16, the second sequencing primer comprises the nucleotide sequence of SEQ ID NO:17, the third sequencing primer comprises the nucleotide sequence of SEQ ID NO:18, and the fourth sequencing primer comprises the nucleotide sequence of SEQ ID NO:19. More preferably, the first sequencing primer consists of the nucleotide sequence of SEQ ID NO:16, the second sequencing primer consists of the nucleotide sequence of SEQ ID NO:17, the third sequencing primer consists of the nucleotide sequence of SEQ ID NO:18, and the fourth sequencing primer consists of the nucleotide sequence of SEQ ID NO:19.

In another preferred embodiment, the method further comprises determining that the first, second, third, or fourth amplicon is respectively specific to an isolate of *Candida albicans*, *Candida glabrata*, *Candida parapsilosis*, or *Candida tropicalis*, based upon the nucleotide sequence of at least the portion of the plus or minus strand of the first, second, third, or fourth amplicon. Preferably, the method further comprises nucleotide sequencing at least a portion of the plus or minus strand of each of at least two amplicons selected from the group consisting of the first, second, third, and fourth amplicons. More preferably, the method further comprises conducting at least two nucleotide sequencing reactions in a single vessel. Most preferably, a sequencing primer is extended in each of the nucleotide sequencing reactions.

In another preferred embodiment, the method further comprises generating a composite nucleotide sequence from all of the nucleotide sequencing reactions. Preferably, the composite nucleotide sequence comprises the nucleotide sequence of SEQ ID NO: 24, SEQ ID NO: 25, SEQ ID NO: 26, SEQ ID NO: 27, SEQ ID NO: 28, or SEQ ID NO: 29. More preferably, the composite nucleotide sequence consists of the nucleotide sequence of SEQ ID NO: 24, SEQ ID NO: 25, SEQ ID NO: 26, SEQ ID NO: 27, SEQ ID NO: 28, or SEQ ID NO: 29.

In another preferred embodiment, the method further comprises determining from the composite nucleotide sequence that the sample contains at least two species of *Candida* selected from the group consisting of *Candida albicans, Candida glabrata, Candida parapsilosis*, and *Candida tropicalis*. Preferably, the method further comprises identifying each of the species of *Candida* present in the sample.

The Second Method of the Present Invention

The second method of the present invention is a method for determining whether a sample contains an isolate of *Candida albicans, Candida glabrata, Candida parapsilosis*, or *Candida tropicalis*, wherein the method comprises (a) providing a vessel containing (1) a nucleic acid from the sample, (2) a primer selected from the group consisting of a first, second, third, and fourth primer, and (3) a fifth primer; wherein the first primer is capable of hybridizing, in a polymerase chain reaction, to at least a portion of a segment of the plus strand of the first amplicon, and wherein the segment consists of nucleotides 240-261 of SEQ ID NO:1; wherein the second primer is capable of hybridizing, in the polymerase chain reaction, to at least a portion of a segment of the plus strand of the second amplicon, and wherein the segment consists of nucleotides 268-298 of SEQ ID NO:3; wherein the third primer is capable of hybridizing, in the polymerase chain reaction, to at least a portion of a segment of the plus strand of the third amplicon, and wherein the segment consists of nucleotides 227-251 of SEQ ID NO:5; wherein the fourth primer is capable of hybridizing, in the polymerase chain reaction, to at least a portion of a segment of the plus strand of the fourth amplicon, and wherein the segment consists of nucleotides 223-247 of SEQ ID NO:7; wherein the fifth primer is capable of hybridizing, in the polymerase chain reaction, to at least a portion of a segment of the minus strand of each of the first, second, third, and fourth amplicons, and wherein the segment consists of nucleotides 242-261 of SEQ ID NO:2, (b) incubating the vessel under conditions allowing production of (1) the first amplicon if the sample contains the isolate of *Candida albicans*, (2) the second amplicon if the sample contains the isolate of *Candida glabrata*, (3) the third amplicon if the sample contains the isolate of *Candida parapsilosis*, or (4) the fourth amplicon if the sample contains the isolate of *Candida tropicalis*, and (c) determining that the sample contains (1) the isolate of *Candida albicans* if the first amplicon is produced in (b), (2) the isolate of *Candida glabrata* if the second amplicon is produced in (b), (3) the isolate of *Candida parapsilosis* if the third amplicon is produced in (b), or (4) the isolate of *Candida tropicalis* if the fourth amplicon is produced in (b); or determining that the sample does not contain any of the isolates of *Candida albicans, Candida glabrata, Candida parapsilosis*, and *Candida tropicalis* if none of the first, second, third, and fourth amplicons are produced in (b).

Advantageously, the first primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters (see below), and the segment consists of nucleotides 240-261 of SEQ ID NO:1; the second primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 268-298 of SEQ ID NO:3; the third primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 227-251 of SEQ ID NO:5; the fourth primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 223-247 of SEQ ID NO:7; and the fifth primer is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 242-261 of SEQ ID NO:2.

In a preferred embodiment, each of the first, second, third, and fourth primers is a forward primer, and the fifth primer is a reverse primer; or each of the first, second, third, and fourth primers is a reverse primer, and the fifth primer is a forward primer. Each of the first, second, third, fourth, and fifth primers preferably is from 8 to 50 nucleotides long, and more preferably is from 12 to 24 nucleotides long.

Preferably, the first primer comprises the nucleotide sequence of SEQ ID NO:9, the second primer comprises the nucleotide sequence of SEQ ID NO:10, the third primer comprises the nucleotide sequence of SEQ ID NO:11, the fourth primer comprises the nucleotide sequence of SEQ ID NO:12, and the fifth primer comprises the nucleotide sequence of SEQ ID NO:13. More preferably, the first primer consists of the nucleotide sequence of SEQ ID NO:9, the second primer consists of the nucleotide sequence of SEQ ID NO:10, the third primer consists of the nucleotide sequence of SEQ ID NO:11, the fourth primer consists of the nucleotide sequence of SEQ ID NO:12, and the fifth primer consists of the nucleotide sequence of SEQ ID NO:13.

In another preferred embodiment, the method further comprises detecting the first, second, third, or fourth amplicon using the oligonucleotide probe described above. Advantageously, the method further comprises isolating the plus or minus strand of the first, second, third, or fourth amplicon. Preferably, the method further comprises determining the nucleotide sequence of at least a portion of the plus or minus strand of the first, second, third, or fourth amplicon. More preferably, the method further comprises determining the nucleotide sequence by conducting a nucleotide sequencing reaction using a sequencing primer capable of hybridizing, in the nucleotide sequencing reaction, to the plus or minus strand of the first, second, third, or fourth amplicon, wherein the sequencing primer is extended during the nucleotide sequencing reaction. Most preferably, the method further comprises determining the nucleotide sequence of at least the portion of the minus strand of the first, second, third, or fourth amplicon respectively using the first, second, third, or fourth sequencing primers described above.

In another preferred embodiment, the method further comprises determining that the first, second, third, or fourth amplicon is respectively specific to an isolate of *Candida albicans, Candida glabrata, Candida parapsilosis*, or *Candida tropicalis*, based upon the nucleotide sequence of at least the portion of the plus or minus strand of the first, second, third, or fourth amplicon. Preferably, the method further comprises nucleotide sequencing at least a portion of the plus or minus strand of each of at least two amplicons selected from the group consisting of the first, second, third, and fourth amplicons. More preferably, the method further comprises conducting at least two nucleotide sequencing reactions in a single vessel. Most preferably, a sequencing primer is extended in each of the nucleotide sequencing reactions.

In another preferred embodiment, the method further comprises generating a composite nucleotide sequence from all of the nucleotide sequencing reactions. Preferably, the composite nucleotide sequence comprises the nucleotide sequence of SEQ ID NO: 24, SEQ ID NO: 25, SEQ ID NO: 26, SEQ ID NO: 27, SEQ ID NO: 28, or SEQ ID NO: 29. More preferably, the composite nucleotide sequence consists of the nucleotide sequence of SEQ ID NO: 24, SEQ ID NO: 25, SEQ ID NO: 26, SEQ ID NO: 27, SEQ ID NO: 28, or SEQ ID NO: 29.

In another preferred embodiment, the method further comprises determining from the composite nucleotide sequence that the sample contains at least two species of *Candida* selected from the group consisting of *Candida albicans, Candida glabrata, Candida parapsilosis*, and *Candida tropicalis*. Preferably, the method further comprises identifying each of the species of *Candida* present in the sample.

The First Composition of the Present Invention

The first composition of the present invention comprises (a) at least two oligonucleotides selected from the group consisting of first, second, third, and fourth oligonucleotides, and (b) a fifth oligonucleotide, wherein the first and fifth oligonucleotides are capable of priming, in a polymerase chain reaction, the synthesis of a first amplicon specific to the isolate of *Candida albicans*, and wherein the first and fifth oligonucleotides are not capable of priming, in the polymerase chain reaction, the synthesis of an amplicon specific to the isolate of *Candida glabrata, Candida parapsilosis*, or *Candida tropicalis*; wherein the second and fifth oligonucleotides are capable of priming, in the polymerase chain reaction, the synthesis of a second amplicon specific to the isolate of *Candida glabrata*, and wherein the second and fifth oligonucleotides are not capable of priming, in the polymerase chain reaction, the synthesis of an amplicon specific to the isolate of *Candida albicans, Candida parapsilosis*, or *Candida tropicalis*; wherein the third and fifth oligonucleotides are capable of priming, in the polymerase chain reaction, the synthesis of a third amplicon specific to the isolate of *Candida parapsilosis*, and wherein the third and fifth oligonucleotides are not capable of priming, in the polymerase chain reaction, the synthesis of an amplicon specific to the isolate of *Candida albicans, Candida glabrata*, or *Candida tropicalis*; wherein the fourth and fifth oligonucleotides are capable of priming, in the polymerase chain reaction, the synthesis of a fourth amplicon specific to the isolate of *Candida tropicalis*, and wherein the fourth and fifth oligonucleotides are not capable of priming, in the polymerase chain reaction, the synthesis of an amplicon specific to the isolate of *Candida albicans, Candida glabrata*, or *Candida parapsilosis*, and wherein the nucleotide sequences of the first, second, third, and fourth amplicons diverge from each other.

In a preferred embodiment, the first oligonucleotide is capable of hybridizing, under highly stringent hybridization conditions (see below), to at least a portion of a segment of the plus strand of the first amplicon, wherein the segment consists of nucleotides 240-261 of SEQ ID NO:1; the second oligonucleotide is capable of hybridizing, under highly stringent hybridization conditions, to at least a portion of a segment of the plus strand of the second amplicon, wherein the segment consists of nucleotides 268-298 of SEQ ID NO:3; the third oligonucleotide is capable of hybridizing, under highly stringent hybridization conditions, to at least a portion of a segment of the plus strand of the third amplicon, wherein the segment consists of nucleotides 227-251 of SEQ ID NO:5; the fourth oligonucleotide is capable of hybridizing, under highly stringent hybridization conditions, to at least a portion of a segment of the plus strand of the fourth amplicon, wherein the segment consists of nucleotides 223-247 of SEQ ID NO:7; and the fifth oligonucleotide is capable of hybridizing, under highly stringent hybridization conditions, to at least a portion of a segment of the minus strand of each of the first, second, third, and fourth amplicons, wherein the segment consists of nucleotides 242-261 of SEQ ID NO:2.

Highly stringent hybridization conditions include at least one of the following conditions: 6X SSC and 65° C; hybridization conditions described in Ausubel et al., 2002, Short Protocols in Molecular Biology, Fifth Edition, Volumes 1 and 2, John Wiley & Sons, Inc., Hoboken, N.J., the entire contents of which are hereby incorporated by reference; and hybridization conditions described in Ausubel et al., 1997, Short Protocols in Molecular Biology, Third Edition, John Wiley & Sons, Inc., New York, N.Y., the entire contents of which are hereby incorporated by reference.

Advantageously, the first oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 240-261 of SEQ ID NO:1; the second oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 268-298 of SEQ ID NO:3; the third oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 227-251 of SEQ ID NO:5; the fourth oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 223-247 of SEQ ID NO:7; and the fifth oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 242-261 of SEQ ID NO:2.

Each of the first, second, third, and fourth amplicons preferably is specific to a ribosomal RNA gene such as a ribosomal RNA gene encoding a 5.8S ribosomal RNA, and more preferably is specific to an internal transcribed spacer of a ribosomal gene such as an internal transcribed spacer 2. Each of the first, second, third, fourth, and fifth oligonucleotides preferably is from 8 to 50 nucleotides long, and more preferably is from 12 to 24 nucleotides long.

Preferably, the first oligonucleotide comprises the nucleotide sequence of SEQ ID NO:9, the second oligonucleotide comprises the nucleotide sequence of SEQ ID NO:10, the third oligonucleotide comprises the nucleotide sequence of SEQ ID NO:11, the fourth oligonucleotide comprises the nucleotide sequence of SEQ ID NO:12, and the fifth oligonucleotide comprises the nucleotide sequence of SEQ ID NO:13. More preferably, the first oligonucleotide consists of the nucleotide sequence of SEQ ID NO:9, the second oligonucleotide consists of the nucleotide sequence of SEQ ID NO:10, the third oligonucleotide consists of the nucleotide sequence of SEQ ID NO:11, the fourth oligonucleotide consists of the nucleotide sequence of SEQ ID NO:12, and the fifth oligonucleotide consists of the nucleotide sequence of SEQ ID NO:13.

In another preferred embodiment, the first composition further comprises a sixth oligonucleotide useful as a probe for detecting the first, second, third, or fourth amplicons. The sixth oligonucleotide preferably is from 15 to 50 nucleotides long, and more preferably is from 25 to 35 nucleotides long.

In another preferred embodiment, the sixth oligonucleotide is capable of hybridizing, under highly stringent hybridization conditions, to at least a portion of a segment of the plus strand of the first amplicon, wherein the segment consists of nucleotides 105-129 of SEQ ID NO:1; the sixth oligonucleotide is capable of hybridizing, under highly stringent hybridization conditions, to at least a portion of a segment of the plus strand of the second amplicon, wherein the segment consists of nucleotides 104-128 of SEQ ID NO:3; the sixth oligonucleotide is capable of hybridizing, under highly stringent hybridization conditions, to at least a portion of a segment of the plus strand of the third amplicon, wherein the segment consists of nucleotides 105-129 of SEQ ID NO:5; and the sixth oligonucleotide is capable of hybridizing, under highly stringent hybridization conditions, to at least a portion of a segment of the plus strand of the fourth amplicon, wherein the segment consists of nucleotides 104-128 of SEQ ID NO:7.

Advantageously, the sixth oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 105-129 of SEQ ID NO:1, nucleotides 104-128 of SEQ ID NO:3, nucleotides 105-129 of SEQ ID NO:5, or nucleotides 104-128 of SEQ ID NO:7.

In another preferred embodiment, the sixth oligonucleotide is capable of hybridizing, under highly stringent hybridization conditions, to at least a portion of a segment of the minus strand of the first amplicon, wherein the segment consists of nucleotides 133-157 of SEQ ID NO:2; the sixth oligonucleotide is capable of hybridizing, under highly stringent hybridization conditions, to at least a portion of a segment of the minus strand of the second amplicon, wherein the segment consists of nucleotides 171-195 of SEQ ID NO:4; the sixth oligonucleotide is capable of hybridizing, under highly stringent hybridization conditions, to at least a portion of a segment of the minus strand of the third amplicon, wherein the segment consists of nucleotides 123-147 of SEQ ID NO:6; and the sixth oligonucleotide is capable of hybridizing, under highly stringent hybridization conditions, to at least a portion of a segment of the minus strand of the fourth amplicon, wherein the segment consists of nucleotides 120-144 of SEQ ID NO:8.

Advantageously, the sixth oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and the segment consists of nucleotides 133-157 of SEQ ID NO:2, nucleotides 171-195 of SEQ ID NO:4, nucleotides 123-147 of SEQ ID NO:6, or nucleotides 120-144 of SEQ ID NO:8.

The sixth oligonucleotide preferably comprises the nucleotide sequence of SEQ ID NO:14 or SEQ ID NO:15, and more preferably consists of the nucleotide sequence of SEQ ID NO:14 or SEQ ID NO:15.

The Second Composition of the Present Invention

A second composition of the present invention comprises (a) a first, second, third, or fourth oligonucleotide, and (b) a fifth oligonucleotide; wherein the first oligonucleotide is capable of hybridizing, under highly stringent hybridization conditions, to at least a portion of a segment of the plus strand of the first amplicon, and wherein the segment consists of nucleotides 240-261 of SEQ ID NO:1; wherein the second oligonucleotide is capable of hybridizing, under highly stringent hybridization conditions, to at least a portion of a segment of the plus strand of the second amplicon, and wherein the segment consists of nucleotides 268-298 of SEQ ID NO:3; wherein the third oligonucleotide is capable of hybridizing, under highly stringent hybridization conditions, to at least a portion of a segment of the plus strand of the third amplicon, and wherein the segment consists of nucleotides 227-251 of SEQ ID NO:5; wherein the fourth oligonucleotide is capable of hybridizing, under highly stringent hybridization conditions, to at least a portion of a segment of the plus strand of the fourth amplicon, and wherein the segment consists of nucleotides 223-247 of SEQ ID NO:7; and wherein the fifth oligonucleotide is capable of hybridizing, under highly stringent hybridization conditions, to at least a portion of a segment of the minus strand of each of the first, second, third, and fourth amplicons, and wherein the segment consists of nucleotides 242-261 of SEQ ID NO:2. Each of the first, second, third, fourth, and fifth oligonucleotides preferably is from 8 to 50 nucleotides long, and more preferably is from 12 to 24 nucleotides long.

Preferably, the first oligonucleotide comprises the nucleotide sequence of SEQ ID NO:9, the second oligonucleotide comprises the nucleotide sequence of SEQ ID NO:10, the third oligonucleotide comprises the nucleotide sequence of SEQ ID NO:11, the fourth oligonucleotide comprises the nucleotide sequence of SEQ ID NO: 12, and the fifth oligonucleotide comprises the nucleotide sequence of SEQ ID NO:13. More preferably, the first oligonucleotide consists of the nucleotide sequence of SEQ ID NO:9, the second oligonucleotide consists of the nucleotide sequence of SEQ ID NO:10, the third oligonucleotide consists of the nucleotide sequence of SEQ ID NO:11, the fourth oligonucleotide consists of the nucleotide sequence of SEQ ID NO:12, and the fifth oligonucleotide consists of the nucleotide sequence of SEQ ID NO:13.

Preferably, the second composition further comprises the sixth oligonucleotide described above.

The Third Composition of the Present Invention

The third composition of the present invention comprises (a) a first, second, third, or fourth oligonucleotide, and (b) a fifth oligonucleotide; wherein the first oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and wherein the segment consists of nucleotides 240-261 of SEQ ID NO:1; wherein the second oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and wherein the segment consists of nucleotides 268-298 of SEQ ID NO:3; wherein the third oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and wherein the segment consists of nucleotides 227-251 of SEQ ID NO:5; wherein the fourth oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and wherein the segment consists of nucleotides 223-247 of SEQ ID NO:7; and wherein the fifth oligonucleotide is at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to, or is 100% identical to the reverse complement of a segment of a polynucleotide based on the Clustal V or W alignment method using the default parameters, and wherein the segment consists of nucleotides 242-261 of SEQ ID NO:2. Each of the first, second, third, fourth, and fifth oligonucleotides preferably is from 8 to 50 nucleotides long, and more preferably is from 12 to 24 nucleotides long.

Preferably, the first oligonucleotide comprises the nucleotide sequence of SEQ ID NO:9, the second oligonucleotide comprises the nucleotide sequence of SEQ ID NO:10, the third oligonucleotide comprises the nucleotide sequence of SEQ ID NO:11, the fourth oligonucleotide comprises the nucleotide sequence of SEQ ID NO:12, and the fifth oligonucleotide comprises the nucleotide sequence of SEQ ID NO:13. More preferably, the first oligonucleotide consists of the nucleotide sequence of SEQ ID NO:9, the second oligonucleotide consists of the nucleotide sequence of SEQ ID NO:10, the third oligonucleotide consists of the nucleotide sequence of SEQ ID NO:11, the fourth oligonucleotide consists of the nucleotide sequence of SEQ ID NO:12, and the fifth oligonucleotide consists of the nucleotide sequence of SEQ ID NO:13.

Preferably, the third composition further comprises the sixth oligonucleotide described above.

BRIEF DESCRIPTION OF THE DRAWINGS

FIG. 2A, FIG. 2C, FIG. 2E, and FIG. 2G: Real-time PCR amplification curves from duplicate ten-fold dilutions of a positive-control plasmid ($10^8$ to $10^2$ or 10 copies per reaction, from left to right) containing the target for *Candida albicans, Candida glabrata, Candida parapsilosis,* and *Candida tropicalis*, respectively. FIG. 2B, FIG. 2D, FIG. 2F, and FIG. 2H: The corresponding standard curves for *Candida albicans, Candida glabrata, Candida parapsilosis,* and *Candida tropicalis*, respectively.

FIG. 3A: Representative real-time PCR amplification curves from reactions using DNA extracted from clinical samples, with *Candida albicans* positive-control plasmid standards (dashed lines; $10^6$, $10^4$, and $10^2$ copies 15 per reaction, from left to right). Figures B through F: Representative pyrograms and resolved sequence (dispensations boxed and corresponding sequence shown below) for *Candida albicans, Candida glabrata, Candida parapsilosis, Candida tropicalis,* and a combination of *Candida albicans* and *Candida parapsilosis* (with sequence from *Candida albicans* in bold and *Candida parapsilosis* in italics), respectively.

DETAILED DESCRIPTION

Figure 1:
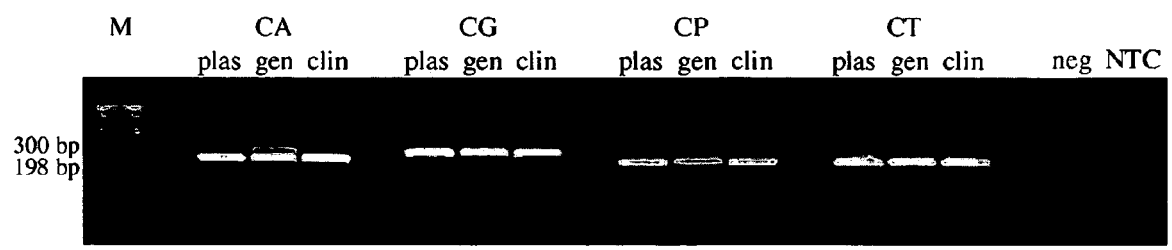
FIG. 1 illustrates agarose gel electrophoresis of real-time PCR products. The end products from real-time PCR amplification with 5 x 10⁶ copies of a positive-control plasmid (plas), 10 ng of DNA extracted from an isolate purchased from ATCC (the American Type Culture Collection, Manassas, Va.) (gen), 0.5 µg of DNA extracted from a positive vaginal sample (confirmed by conventional PCR, clin) of each *Candida* species (CA=*Candida albicans*, CG=*Candida glabrata*, CP=*Candida parapsilosis*, CT=*Candida tropicalis*), 0.5 µg of DNA extracted from a negative vaginal sample (confirmed by conventional PCR, neg), and nuclease and pyrogen-free water (NTC) as a template were analyzed on a 2% agarose gel containing 0.5 µg/ml ethidium bromide.

The following examples illustrate the use of four pairs of oligonucleotide primers to generate four *Candida*-specific amplicons in polymerase chain reactions using nucleic acid isolated from biological samples as templates. Each of these pairs of oligonucleotides primed 25 the synthesis of an amplicon specific to only one of the following species: *Candida albicans, Candida glabrata, Candida parapsilosis,* and *Candida tropicalis*. The forward primers of the four primer pairs have identical nucleotide sequences, while each reverse primer has a unique sequence relative to the other three reverse primers. This divergence is responsible for the specificity of the resultant amplicon. These examples also illustrate the use of an 30. oligonucleotide probe which detected each of the four amplicons. Finally, these examples illustrate the use of four oligonucleotides as nucleotide sequencing primers, wherein each sequencing primer is specific to one of the four amplicons. Each of these sequencing primers was used in a nucleotide sequencing reaction to confirm that the respective amplicon was specific to *Candida albicans, Candida glabrata, Candida parapsilosis,* or *Candida tropicalis*. These examples are set forth by way of illustration only, and nothing therein shall be taken as a limitation upon the overall scope of the invention.

EXAMPLES

Clinical Samples and DNA Extraction

A total of 231 vaginal samples from female subjects were tested. The subjects' symptoms, HIV status, and clinician diagnoses were not disclosed. Patient care providers collected specimens from a vaginal sampling using a Cellmatics swab (BD, Sparks, Md.), which was then placed in 2 ml of its accompanying transport medium. Upon receipt, swabs were immediately processed for analysis by PCR. Established procedures for SDS/proteinase K lysis and phenol/chloroform DNA extraction from 470 µl of swab transport media were used (see Ausubel et al., 1997, Short Protocols in Molecular Biology, Third Edition, John Wiley & Sons, Inc., New York, N.Y.). DNA concentration was calculated by absorbance 260/280 readings and was adjusted to 0.2 µg/µl prior to PCR analysis.

Conventional PCR Assay

The primers utilized for species-specific amplification of *Candida* ribosomal DNA and reaction conditions were previously described (see Luo et al., 2002, Rapid identification of pathogenic fungi directly from cultures by using multiplex PCR, J Clin Microbiol 40:2860-2865). All PCR reactions were carried out with 1 µg of extracted DNA in 50 µl total volume and were analyzed by electrophoresis through a 2% agarose gel containing 0.5 µg/ml ethidium bromide. Positive controls consisted of DNA extracted from *Candida albicans, Candida glabrata, Candida parapsilosis,* and *Candida tropicalis* purchased from ATCC. Negative controls consisted of the substitution of nuclease and pyrogen-free water for DNA. 100% specificity and 100% sensitivity of these PCR amplifications were previously reported (see Luo et al., 2002, Rapid identification of pathogenic fungi directly from cultures by using multiplex PCR, J Clin Microbiol 40:2860-2865). Additionally, PCR amplifications with each primer pair exhibited no cross-reactivity among the four *Candida* species or a panel of genomic DNA extracted from 34 different bacterial, viral, and fungal pathogens (data not shown).

Primer and Fluorescent Probe Design

All primers, probes, and modifications were synthesized by Integrated DNA Technologies (IDT, Coralville, Iowa). Sequences for the internal transcribed spacer 2 (ITS2) region flanked by the 5.8S and 28S rDNAs of *Candida albicans, Candida glabrata, Candida parapsilosis, Candida tropicalis,* and *Saccharomyces cerevisiae* (GenBank accession numbers L07796, AF218994, L11352, L47112, and AJ275936, respectively) were aligned using MegAlign version 5.51 software (Lasergene suite, DNASTAR Inc., Madison, Wis.). The sequence of the real-time PCR and Pyrosequencing primers and probes are listed in Table 1 (see below). Successful amplification of *Candida albicans, Candida glabrata, Candida parapsilosis,* or *Candida tropicalis* resulted in a 261 bp, 298 bp, 251 bp, or 249 bp product, respectively (see FIG. 1). Sequencing primers were selected within the regions amplified by the PCR primers for each of the four *Candida* species.

TABLE 1

Primers and Probes for *Candida* Real-Time PCR and Pyrosequencing.

| Method | Function | Name | Sequence |
|---|---|---|---|
| Real-Time PCR | Primer | bio-ITS3[1] | 5'-bio[2]-gcatcgatgaagaacgcagc-3' (SEQ ID NO: 13 with the addition of the bio moiety) |
| | | CA-SHIN[3] | 5'-ggacgttaccgccgcaagcaat-3' (SEQ ID NO: 9) |
| | | CG-JPT2L | 5'-ccgagttggtaaaacctaatacagtattaac-3' (SEQ ID NO: 10) |

TABLE 1-continued

Primers and Probes for *Candida* Real-Time PCR and Pyrosequencing.

| Method | Function | Name | Sequence |
|---|---|---|---|
| | | CP-SHIN[3] | 5'-tggaagaagttttggagtttgtacc-3'<br>(SEQ ID NO: 11) |
| | | CT-SHIN[3] | 5'-ggccactagcaaaataagcgttttg-3'<br>(SEQ ID NO: 12) |
| | Probe | CANFAM[3] | 5'-6-FAM[4]-aaaygacgctcaaacaggcatgccc-BHQ1[5]-3'<br>(SEQ ID NO: 14 with the addition of the 6-FAM and BHQ1 moieties) |
| Pyrosequencing Primer | | CA-MOD | 5'-acgttaccgccgcaagcaat-3'<br>(SEQ ID NO: 16) |
| | | CG-seq1 | 5'-cgagttggtaaaacctaata-3'<br>(SEQ ID NO: 17) |
| | | CP-SHIN[3] | 5'-tggaagaagttttggagtttgtacc-3'<br>(SEQ ID NO: 18) |
| | | CT-MOD | 5'-ggccactagcaaaataagcgt-3'<br>(SEQ ID NO: 19) |

[1]Redesigned from a previously described primer (see White et al., 1990, Amplification and direct sequencing of fungal ribosomal RNA genes for phylogenetics, in: M.A. Innis, D.H. Helfand, J.J. Sninsky, and T.J. White (Eds.), PCR protocols, Academic Press, Inc., San Diego, CA, pp. 315-322).
[2]5' biotin modification.
[3]Redesigned from a previously described primer (see Shin et al., 1999, Rapid identification of up to three *Candida* species in a single reaction tube by a 5' exonuclease assay using fluorescent DNA probes, J Clin Microbiol 37:165-170).
[4]5' 6-carboxy-fluorescein modification.
[5]3' Black Hole Quencher 1 modification.

Positive-Control Plasmids

Positive controls for each *Candida* species were generated by subcloning amplicons derived from the use of the ITS3 and ITS4 universal fungal primer pair (see White et al., 1990, Amplification and direct sequencing of fungal ribosomal RNA genes for phylogenetics, in: M. A. Innis, D. H. Helfand, J. J. Sninsky, and T. J. White (Eds.), PCR protocols, Academic Press, Inc., San Diego, pp. 315-322) and template DNA extracted from *Candida albicans, Candida glabrata, Candida parapsilosis*, and *Candida tropicalis* ATCC-purchased controls. Amplicons were subcloned into the pCRII-TOPO vector of the TOPO TA Cloning Dual Promoter kit (Invitrogen, Carlsbad, Calif.) according to the manufacturer's instructions. DNA concentration was calculated by 260/280 absorbance readings.

Real-Time PCR Assay

Each 25 µl reaction contained 0.5 µg of extracted DNA, 300 nM each of bio-ITS3, CA-SHIN, CG-JPT2L, CP-SHIN, and CT-SHIN, 200 nM of CANFAM, and 12.5 µl of 2X concentration Platinum Quantitative PCR Supermix-UDG (Invitrogen, Carlsbad, Calif.). The real-time PCR reactions were performed on a Rotor-Gene 3000 instrument (Corbett Research, Sydney, Australia) and included an initial incubation at 50° C. for 2 minutes followed by 95° C. for 2 minutes. Next, 45 cycles of denaturation (95° C., 20 seconds) and annealing/extension (60° C., 60 seconds) were performed with fluorescence acquisition (470 nM source/510 nM detection) immediately following each annealing/extension step. A final extension (72° C., 10 minutes) was performed. Positive controls consisted of positive-control plasmid DNA at $10^6$, $10^4$, and $10^2$ copies per reaction. Negative controls consisted of the substitution of nuclease and pyrogen-free water for DNA. Normalized fluorescence was analyzed on the Rotor-Gene 3000 Software, Version 5 (Build 47) with dynamic tube normalization and slope correction.

Pyrosequencing

For PCR product purification prior to Pyrosequencing analysis, the bio-ITS3 primer (see Table 1) was synthesized with a 5' biotin modification which was incorporated into the amplicon during the amplification process. The biotinylated PCR product was captured with streptavidin Sephadex (Amersham Biosciences, Uppsala, Sweden), then purified and denatured with a vacuum prep workstation according to the manufacturer's instructions (Biotage, Uppsala, Sweden). For the Pyrosequencing reaction, 0.5 µM of each sequencing primer in the sequencing primer pool (see Table 1) was utilized to prime the biotinylated amplification products. A Pyrosequencing 96MA System (Biotage, Uppsala, Sweden) was programmed with 10 cycles of an AGCT dispensation order. The resulting Pyrosequencing data, termed "pyrograms," were analyzed with the PSQ 96MA version 2.0.2 software. The best quality DNA sequence resolved was used in subsequent analyses.

Analysis of Real-Time PCR Conditions

To confirm amplification quality, the real-time PCR products generated from $5 \times 10^6$ copies of the positive-control plasmid, 10 ng of DNA extracted from an isolate purchased from ATCC, and 0.5 µg of DNA extracted from a positive vaginal sample (confirmed by conventional PCR) of each *Candida* species were subjected to agarose gel electrophoresis (see FIG. 1). The product generated from each template type was a single band of the expected size and lacked the formation of any primer dimers. This indicates the ability of the real-time PCR to efficiently amplify a specific target not only from the positive-control plasmids, but also from more complex DNAs (isolated Candida genomic DNA) and mixtures of complex DNAs (DNA extracted from a vaginal sample). To further validate the specificity of the real-time PCR, DNA was extracted from 42 potentially cross-reacting human pathogens of bacterial, viral, and fungal origin, including potentially cross-reacting *Candida, Aspergillus*, and *Saccharomyces* species purchased from ATCC. Two hundred nanograms of genomic DNA from each pathogen were examined under test conditions for cross-reactivity and none was observed (data not shown).

Figure 2:
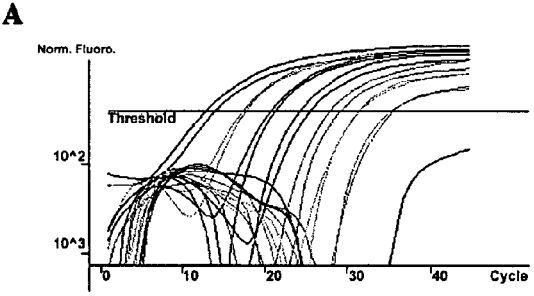
FIG. 2 illustrates a positive-control plasmid DNA standard curve for real-time PCR.
Figure 2:
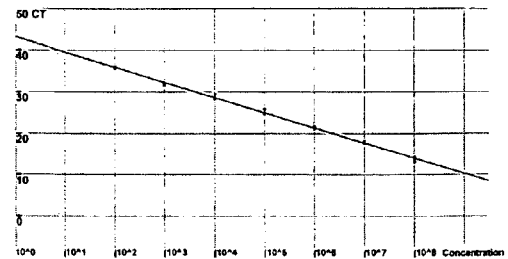
Figure 2:
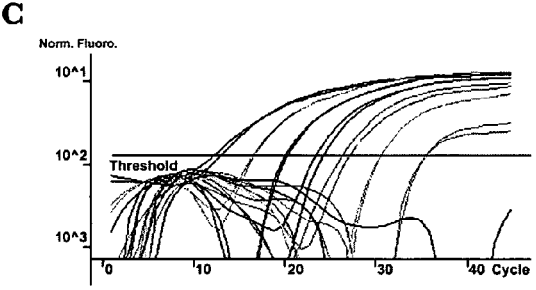
Figure 2:
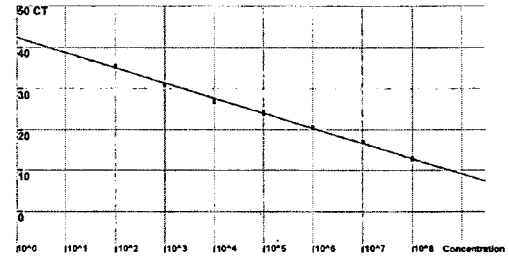
Figure 2:
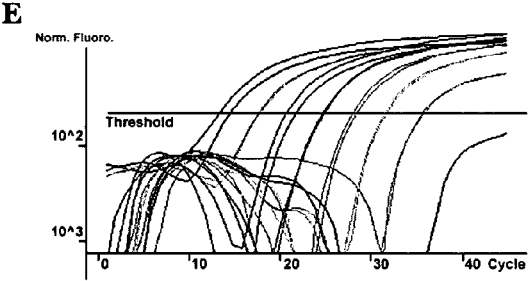
Figure 2:
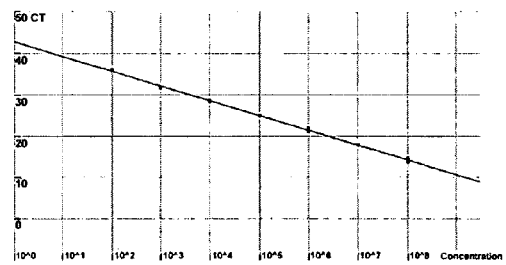
Figure 2:
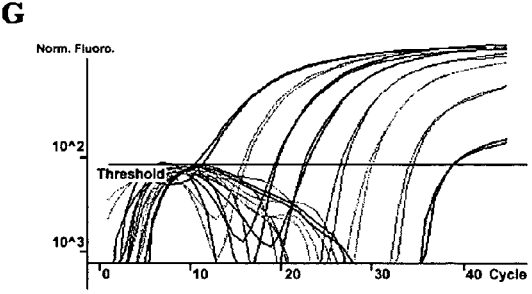
Figure 2:
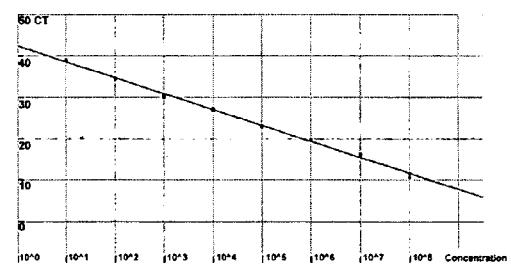

To determine the sensitivity of the real-time PCR for the target, the positive-control plasmid was ten-fold serially diluted from $10^8$ to ten copies and each dilution added as a template to duplicate PCR reactions (see FIG. 2). The linear detection range for the *Candida albicans, Candida glabrata*, and *Candida parapsilosis* plasmids was from $10^8$ to 100 copies per reaction with $r^2$ values of 0.995, 0.995, and 0.998, respectively. The linear detection range for the Candida tropicalis plasmid was from 108 to ten copies per reaction with an $r^2$ value of 0.996. To verify that components of a clinical vaginal sample DNA extraction do not alter the efficiency of detection, 0.5 µg of a *Candida*-negative DNA extract (confirmed by conventional PCR) were added to PCR reactions of each positive-control plasmid dilution series. In their respective linear ranges, no significant difference in CT score was apparent between the presence and absence of the vaginal DNA extract (data not shown).

Analysis of Pyrosequencing Conditions

To determine the ability of the primer pool to specifically discriminate among the four *Candida* species, 0.2 µg of genomic DNA extracts from *Candida albicans, Candida glabrata, Candida parapsilosis, Candida tropicalis, Candida krusei*, and *Saccharomyces cerevisiae* isolates purchased from ATCC were amplified in separate real-time PCR reactions using the PCR primer and probe pool (see Table 1). The products of each PCR reaction were then sequenced using the Pyrosequencing primer pool (see Table 1). Sequences obtained from *Candida albicans, Candida glabrata, Candida parapsilosis*, and *Candida tropicalis* were identical to the expected sequences shown in Table 2 (see below), except for the stretch of 6 A's in *Candida parapsilosis*, which was occasionally resolved as 5 A's. The resolution of homopolymeric stretches is a known limitation of the Pyrosequencing technique (see Ronaghi et al., 1998, A sequencing method based on real-time pyrophosphate, Science 281:363-365). No readable sequence was obtained from *Candida krusei* or *Saccharomyces cerevisiae*. To determine the minimum copy number initially present in a PCR reaction necessary to generate readable sequence, PCR products of each positive-control plasmid dilution series (as in FIG. 2) were sequenced with the Pyrosequencing primer pool. Readable sequence was obtained for all four species with as few as 100 copies of positive-control plasmid initially present in the PCR reaction (data not shown). The lengths of the best quality sequences were significantly shorter than those from purified genomic DNA, but provided enough sequence (*Candida albicans*, 15 nucleotides; *Candida glabrata*, 18 nucleotides; *Candida parapsilosis*, 8 nucleotides; and *Candida tropicalis*, 12 nucleotides) to differentiate the four *Candida* species by identity to the expected sequences.

TABLE 2

Expected DNA Sequences for Pyrosequencing Identification of Candida Species.

| Species | Sequence (reverse complement)[1] |
|---|---|
| Candida albicans | $GT_5/G_2T_2/AG/AC_2T/A_2GC_2/AT_2/GT/C/A_3GC/G$ (i.e., 5'-gtttttggttagacctaagccattgtcaaagcg-3'; SEQ ID NO: 20) |
| Candida glabrata | $C/AGT/AT_2/A_2C_5/GC_2/GCT/C/GC/GC/A_3C$ (i.e., 5'-cagtattaaccccgccgctcgcgcaaac-3'; SEQ ID NO: 21) |
| Candida parapsilosis | $A_2T/G/AGT/G_2/A_6C_2T/AT/C_2/AT_2/AGT_3/AT$ (i.e., 5'-aatgagtggaaaaaacctatccattagtttat-3'; SEQ ID NO: 22) |
| Candida tropicalis | $T_3/G_2/AT/A_3C_2T/A_2GT/C/GCT_2/A_4T/A_2GT_3/C_2$ (i.e., 5'-tttggataaacctaagtcgcttaaaataagtttcc-3'; SEQ ID NO: 23) |
| Candida albicans + Candida glabrata | $GCT_5/AG_3T_3/A_2GT_2/A_3C_7T/A_2G_2C_4/AGCT_3/GCT/GC_2/A_3G_2C_2/A_3GC$ (i.e., 5'-gcttttagggtttaagttaaacccccctaaggcccagctttgct gccaaaggccaaagc-3'; SEQ ID NO: 24) |
| Candida albicans + Candida parapsilosis | $A_2GT_6/G_3T_2/A_2G_2T/AG_2C_2T/A_8GC_4T/A_2T_3/GC_2T/ACT_2/A_4G_2CT_3/AGT$ (i.e., 5'-aagttttttggggttaaggtaggcctaaaaaaaagcccctaatttgcc tacttaaaaggctttagt-3'; SEQ ID NO: 25) |
| Candida albicans + Candida tropicalis | $GT_8/G_4T_2/A_2GT/A_4C_4T_2/A_4G_2C_2T/ACT_2/G_2CT_3/A_4CT/A_5G_2CT_3/GC_2$ (i.e., 5'-gttttttttgggggttaagtaaaaccccttaaaaggcctacttggctt taaaactaaaaaggctttgcc-3'; SEQ ID NO: 26) |

TABLE 2-continued

Expected DNA Sequences for Pyrosequencing Identification of
Candida Species.

| Species | Sequence (reverse complement)[1] |
|---|---|
| Candida glabrata + Candida parapsilosis | $A_2CT/AG_2T/A_2GT_3/A_2G_2C_5/A_6GC_4T/AGCT_2/C_3/AGCT_2/AG_2CT_3/A_4CT$ (i.e., 5'-aactaggtaagtttaaggccccaaaaaagccctagcttcccagct taggctttaaaact-3'; SEQ ID NO: 27) |
| Candida glabrata + Candida tropicalis | $CT_3/AG_3T/A_2T_3/A_5C_7T/A_2G_2C_2T/GC_2T/GC_2T_2/A_4GCT/A_2G_2CT_3/A_3C_3$ (i.e., 5'-ctttagggtaatttaaaaaccccccctaaggcctgcctgccttaaaa gctaaggctttaaaccc-3': SEQ ID NO: 28) |
| Candida parapsilosis + Candida tropicalis | $A_2T_4/G_3/A_2GT_2/A_3G_2C_2T/A_8GC_2T_2/ACT/GC_3T_2/A_5T_3/A_3G_2T_6/AC_2T$ (i.e., 5'-aattttgggaagttaaaggcctaaaaaaaagccttactgcccttaaa aatttaaaggtttttttacct-3'; SEQ ID NO: 29) |

[1]Subscript numbers indicate the number of repeats of the preceding nucleotide in the expected sequence. Slashes divide the expected sequence by Pyrosequencing AGCT nucleotide dispensation cycles.

Clinical Application of the Real-Time PCR and Pyrosequencing Assay

To access the quality of the real-time PCR and Pyrosequencing method for identifying *Candida* species from clinical samples, DNA extracts from 231 vaginal samples were analyzed. Typical real-time PCR (see FIG. 3A) and Pyrosequencing results (see FIG. 3B through F) from clinical samples were similar to the results obtained from genomic DNA isolated from purified *Candida* isolates. The lengths of the best quality sequences resolved from the pyrograms of clinical samples were usually shorter than those from purified genomic DNA, but provided enough sequence to differentiate the four *Candida* species by identity to the expected sequences.

Figure 3:
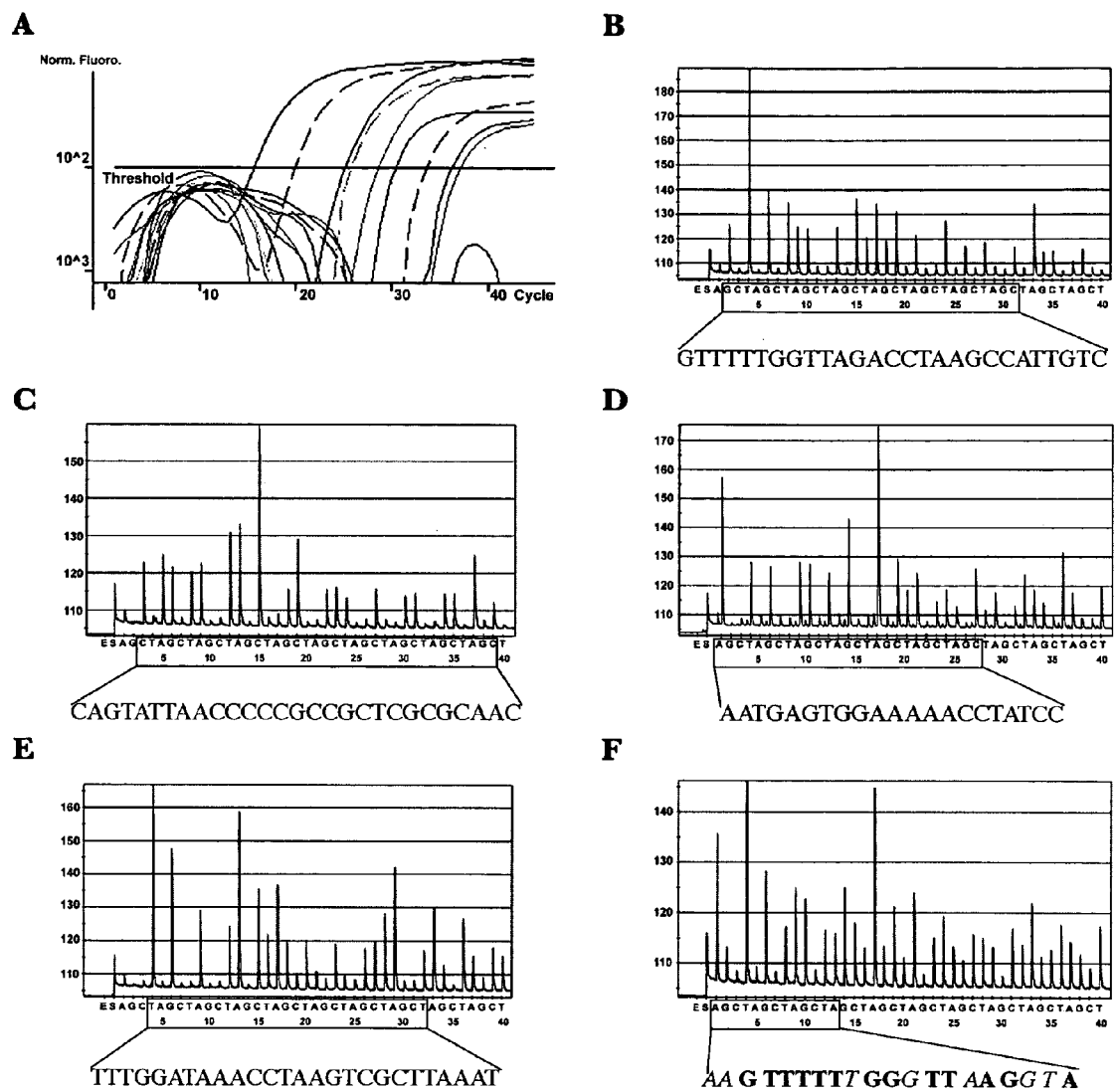
FIG. 3 illustrates real-time PCR and pyrosequencing identification of *Candida* species in DNA extracted from vaginal samples.

To assist in rapid speciation, sequencing primers and the nucleotide dispensation order were chosen to provide easily identifiable pyrogram patterns within the first dispensation cycle. As expected from Table 2, each sequence generated species-specific peaks within the first cycle of four nucleotide dispensations: *Candida albicans* is identified by a G and T peak (see FIG. 3B), *Candida glabrata* is identified by a C peak (see FIG. 3C), *Candida parapsilosis* is identified by an A and T peak (see FIG. 3D), and *Candida tropicalis* is identified by a T peak (see FIG. 3E). As shown in FIG. 3F, it is also possible to resolve the sequences of two *Candida* species present in a clinical sample by inspection of the pyrogram. The A, G, and T peaks in the first cycle of four nucleotide dispensations positively identify a combination of *Candida albicans* and *Candida parapsilosis*. As shown in Table 2, a combination of *Candida albicans* and *Candida tropicalis* is not as easily identified in the first dispensation cycle due to similarities with *Candida albicans*. However, a T peak in the third dispensation cycle (dispensation 12), which is absent in *Candida albicans*, positively identifies a combination of *Candida albicans* and *Candida tropicalis*.

To access the specificity and sensitivity of the real-time PCR and Pyrosequencing method for identifying *Candida* species from clinical samples, the results were compared to those obtained from conventional PCR identification of *Candida albicans, Candida glabrata, Candida parapsilosis*, and *Candida tropicalis*. The two PCR-based methods amplify different regions of the rDNA. As shown in Table 3 (see below), the real-time PCR method generated no false negatives or false positives with respect to the absence (96/96) or presence of DNA from any of the four *Candida* species (135/135). When speciated by Pyrosequencing, results from 133 of the 135 positive samples agreed. The two discordant samples were found to contain *Candida albicans* by both identification methods, but the sequencing data obtained from Pyrosequencing unambiguously identified a second *Candida* species. One sample contained both *Candida albicans* and *Candida parapsilosis* (see FIG. 3F) and the other contained both *Candida albicans* and *Candida tropicalis*. A separate species-specific real-time PCR (see Shin et al., 1999, Rapid identification of up to three *Candida* species in a single reaction tube by a 5' exonuclease assay using fluorescent DNA probes, J Clin Microbiol 37:165-170) confirmed the presence of the second species in both samples and agreed with the Pyrosequencing results (data not shown).

TABLE 3

Agreement of Real-Time PCR and Pyrosequencing with Conventional PCR for *Candida* Species Identification.

| | | CONVENTIONAL PCR | | | | | | |
|---|---|---|---|---|---|---|---|---|
| | | NEG[1] | CA[2] | CG[3] | CP[4] | CT[5] | CA + CP | CA + CT | TOTAL |
| REAL-TIME PCR AND PYROSEQUENCING | NEG | 96 | | | | | | | 96 |
| | CA | | 67 | | | | | | 67 |
| | CG | | | 32 | | | | | 32 |
| | CP | | | | 18 | | | | 18 |
| | CT | | | | | 13 | | | 13 |

TABLE 3-continued

Agreement of Real-Time PCR and Pyrosequencing with Conventional PCR for *Candida* Species Identification.

| | CONVENTIONAL PCR | | | | | | | |
|---|---|---|---|---|---|---|---|---|
| | | NEG[1] | CA[2] | CG[3] | CP[4] | CT[5] | CA + CP | CA + CT | TOTAL |
| CA + CP | | | 1 | | | | 2 | | 3 |
| CA + CT | | | 1 | | | | | 1 | 2 |
| TOTAL | | 96 | 69 | 32 | 18 | 13 | 2 | 1 | 231 |

[1]NEG = negative
[2]CA = *Candida albicans*
[3]CG = *Candida glabrata*
[4]CP = *Candida parapsilosis*
[5]CT = *Candida tropicalis*

The invention claimed is:

1. A method for determining whether a vaginal Sample contains an isolate of *Candida albicans, Candida glabrata, Candida parapsilosis*, or *Candida tropicalis*, comprising the steps of:
   (a) providing a vessel containing (1) a nucleic acid from the sample, (2) at least two primers selected from the group consisting of first, second, third, and fourth primers, and (3) a fifth primer, wherein the first primer consists of nucleotide sequence of SEQ ID NO: 9, the second primer consists of nucleotide sequence of SEQ ID NO: 10, the third primer consists of nucleotide sequence of SEQ ID NO: 11, the fourth primer consists of nucleotide sequence of SEQ ID NO: 12, and the fifth primer consists of nucleotide sequence of SEQ ID NO: 13,
   wherein the first and fifth primers prime, in a polymerase chain reaction, the synthesis of a first amplicon specific to the isolate of *Candida albicans*, and wherein the First and fifth primers do not prime, in the polymerase chain reaction, the synthesis of an amplicon specific to the isolate of *Candida glabrata, Candida parapsilosis*, or *Candida tropicalis*,
   wherein the second and fifth primers prime, in the polymerase chain reaction, the synthesis of a second amplicon specific to the isolate of *Candida glabrata*, and wherein the second and fifth primers do not prime, in the polymerase chain reaction, the synthesis of an amplicon specific to the isolate of *Candida albicans, Candida parapsilosis*, or *Candida tropicalis*,
   wherein the third and fifth primers prime, in the polymerase chain reaction, the synthesis of a third amplicon specific to the isolate of *Candida parapsilosis*, and wherein the third and fifth primers do not prime, in the polymerase chain reaction, the synthesis of an amplicon specific to the isolate of *Candida albicans, Candida glabrata*, or *Candida tropicalis*,
   wherein the fourth and fifth primers prime, in the polymerase chain reaction, the synthesis of a fourth amplicon specific to the isolate of *Candida tropicalis*, and wherein the fourth and fifth primers do not prime, in the polymerase chain, reaction, the synthesis of an amplicon specific to the isolate of *Candida albicans, Candida glabrata*, or *Candida parapsilosis*,
   wherein the nucleotide sequences of the first, second, third, and fourth amplicons diverge from each other;
   (b) incubating the vessel under conditions allowing production of (1) the first amplicon if the sample contains the isolate of *Candida albicans*, (2) the second amplicon if the sample contains the isolate of *Candida glabrata*, (3) the third amplicon if the sample contains the isolate of *Candida parapsilosis*, or (4) the fourth amplicon if the sample contains the isolate of *Candida tropicalis*,
   wherein the first primer hybridizes to at least a portion of a segment of the plus strand of the first amplicon, and wherein the segment consists of nucleotides 240-261 of SEQ ID NO:1,
   wherein the second primer hybridizes to at least a portion of a segment of the plus strand of the second amplicon, and wherein the segment consists of nucleotides 268-298 of SEQ ID NO:3,
   wherein the third primer hybridizes to at least a portion of a segment of the plus strand of the third amplicon, and wherein the segment consists of nucleotides 227-251 of SEQ NO:5,
   wherein the fourth primer hybridizes to at least a portion of a segment of the plus strand of the fourth amplicon, and wherein the segment consists of nucleotides 223-247 of SEQ ID NO:7, and
   wherein the fifth primer hybridizes to at least a portion of a segment of the minus strand of each of the first, second, third, and fourth amplicons, and wherein the segment consists of nucleotides 242-261 of SEQ ID NO:2;
   (c) pyrosequencing the first, second, third and fourth amplicons using nucleotide dispensation, wherein said pyrosequencing generates species-specific peaks, and whereby *Candida albicans* is identified by a G and T peak, *Candida glabrata* is identified by a C peak, *Candida parapsilosis* is identified by an A and T peak, and *Candida tropicalis* is identified by a T peak; and
   (d) determining that the sample contains (1) the isolate of *Candida albicans* if the first amplicon is produced in (b), (2) the isolate of *Candida glabrata* if the second amplicon is produced in (b), (3) the isolate of *Candida parapsilosis* if the third amplicon is produced in (b), or (4) the isolate of *Candida tropicalis* if the fourth amplicon is produced in (b); or determining that the sample does not contain any of the isolates of *Candida albicans, Candida glabrata, Candida parapsilosis*, and *Candida tropicalis* if none of the first, second, third, and fourth amplicons are produced in (b).

2. The method of claim 1, wherein the first primer comprises the nucleotide sequence of SEQ ID NO: 9, wherein the second primer comprises the nucleotide sequence of SEQ ID NO: 10, wherein the third primer comprises the nucleotide sequence of SEQ ID NO: 11, wherein the fourth primer comprises the nucleotide sequence of SEQ ID NO: 12, and wherein the fifth primer comprises the nucleotide sequence of SEQ ID NO: 13.

3. The method of claim 2, wherein the first primer consists of the nucleotide sequence of SEQ ID NO: 9, wherein the second primer consists of the nucleotide sequence of SEQ ID NO: 10, wherein the third primer consists of the nucleotide sequence of SEQ ID NO: 11, wherein the fourth primer consists of the nucleotide sequence of SEQ ID NO: 12, and wherein the fifth primer consists of the nucleotide sequence of SEQ ID NO: 13.

4. The method of claim 1, in step (a) and prior to step (b), further comprising a step of:
   (a') adding an oligonucleotide probe, wherein the oligonucleotide probe detects the first, second, third, or fourth amplicon.

5. The method of claim 4, wherein the oligonucleotide probe comprises the nucleotide sequence of SEQ ID NO: 14 or SEQ ID NO: 15.

6. The method of claim 5, wherein the oligonucleotide probe consists of the nucleotide sequence of SEQ ID NO: 14 or SEQ ID NO: 15.

7. The method of claim 1, further comprising isolating the plus or minus strand of the first, second, third, or fourth amplicon.

8. The method of claim 7, further comprising determining the nucleotide sequence of at least a portion of the plus or minus strand of the first, second, third, or fourth amplicon.

9. The method of claim 8, further comprising determining the nucleotide sequence by conducting a nucleotide sequencing reaction using a sequencing primer that hybridizes, in the nucleotide sequencing reaction, to the plus or minus strand of the first, second, third, or fourth amplicon, wherein the sequencing primer is extended during the nucleotide sequencing reaction.

10. The method of claim 9, further comprising determining the nucleotide sequence of at least the portion of the minus strand of the first, second, third, or fourth amplicon using a first, second, third, or fourth sequencing primer, respectively.

11. The method of claim 9, wherein the sequencing primer is from 8 to 30 nucleotides long.

12. The method of claim 10, wherein the first sequencing primer hybridizes, in the nucleotide sequencing reaction, to at least a portion of a segment of the plus strand of the first amplicon, and wherein the segment consists of nucleotides 240-259 of SEQ ID NO: 1, wherein the second sequencing primer hybridizes, in the nucleotide sequencing reaction, to at least a portion of a segment of the plus strand of the second amplicon, and wherein the segment consists of nucleotides 278-297 of SEQ ID NO: 3, wherein, the third sequencing primer hybridizes, in the nucleotide sequencing reaction, to at least a portion of a segment of the plus strand of the third amplicon, and wherein the segment consists of nucleotides 227-251 of SEQ ID NO:5, and wherein the fourth sequencing primer hybridizes, in the nucleotide sequencing reaction, to at least a portion of a segment of the plus strand of the fourth amplicon, and wherein the segment consists of nucleotides 227-247 of SEQ ID NO: 7.

13. The method of claim 10, wherein the first sequencing primer comprises the nucleotide sequence of SEQ ID NO: 16, wherein the second sequencing primer comprises the nucleotide sequence of SEQ ID NO: 17, wherein the third sequencing primer comprises the nucleotide sequence of SEQ ID NO: 18 and wherein the fourth sequencing primer comprises the nucleotide sequence of SEQ ID NO: 19.

14. The method of claim 13, wherein the first sequencing primer consists of the nucleotide sequence of SEQ ID NO: 16, wherein the second sequencing primer consists of the nucleotide sequence of SEQ ID NO: 17, wherein the third sequencing primer consists of the nucleotide sequence of SEQ ID NO: 18, and wherein the fourth sequencing primer consists of the nucleotide sequence of SEQ ID NO: 19.

15. The method of claim 8, further comprising determining that the first, second, third, or fourth amplicon is respectively specific to an isolate of *Candida albicans, Candida glabrata, Candida parapsilosis*, or *Candida tropicalis*, based upon the nucleotide sequence of at least the portion of the plus or minus strand of the first, second, third, or fourth amplicon.

16. The method of claim 7, further comprising nucleotide sequencing at least a portion of the plus or minus strand of each of at least two amplicons selected from the group consisting of the first, second, third, and fourth amplicons.

17. The method of claim 16, further comprising conducting at least two nucleotide sequencing reactions in a single vessel.

18. The method of claim 17, further comprising extending a sequencing primer in each of the nucleotide sequencing reactions.

19. The method of claim 17, further comprising generating a composite nucleotide sequence from all of the nucleotide sequencing reactions.

20. The method of claim 19, wherein the composite nucleotide sequence comprises the nucleotide sequence of SEQ ID NO: 24, SEQ ID NO: 25, SEQ ID NO: 26, SEQ ID NO: 27, SEQ ID NO: 28 or SEQ ID NO: 29.

21. The method of claim 20, wherein the composite nucleotide sequence consists of the nucleotide sequence of SEQ ID NO: 24, SEQ ID NO: 25, SEQ ID NO: 26, SEQ ID NO: 27, SEQ ID NO: 28, or SEQ ID NO: 29.

22. The method of claim 19, further comprising determining from the composite nucleotide sequence that the sample contains at least two species of *Candida* selected from the group consisting of *Candida albicans, Candida glabrata, Candida parapsilosis*, and *Candida tropicalis*.

23. The method of claim 2, further comprising identifying each of the species of *Candida* present in the sample.

* * * * *